United States Patent [19]  
Atchley

[11] 4,451,257  
[45] May 29, 1984

[54] SURGICAL ASPIRATOR WITH POPPET CONTROL VALVE

[76] Inventor: Frank W. Atchley, P.O. Box 2730, Napa, Calif. 94558

[21] Appl. No.: 316,297

[22] Filed: Oct. 29, 1981

[51] Int. Cl.³ .............................................. A61M 1/00
[52] U.S. Cl. .................................. 604/119; 604/902; 604/33; 433/95; 251/325
[58] Field of Search ..................... 604/33, 35, 40, 43, 604/93, 118, 119, 164, 165, 166, 170, 902, 27, 42; 137/243; 251/324, 325; 285/7; 15/418; 433/95, 100

[56] References Cited

U.S. PATENT DOCUMENTS

| | | | |
|---|---|---|---|
| 2,712,950 | 7/1955 | Siebert | 285/7 |
| 3,090,396 | 5/1963 | Rudelick | 251/324 |
| 3,159,378 | 12/1964 | Haag | 251/325 |
| 3,426,759 | 2/1969 | Smith | 604/902 |
| 3,929,126 | 12/1975 | Corsaut | 604/40 |
| 3,950,014 | 4/1976 | Doubleday | 285/7 |
| 4,134,573 | 1/1979 | Messinger | 251/324 |
| 4,193,406 | 3/1980 | Jinotti | 604/33 |
| 4,212,300 | 7/1980 | Meals | 604/119 |

FOREIGN PATENT DOCUMENTS

| | | | |
|---|---|---|---|
| 835259 | 3/1952 | Fed. Rep. of Germany | 251/325 |
| 29038 | of 1914 | United Kingdom | 15/418 |

Primary Examiner—C. Fred Rosenbaum  
Assistant Examiner—J. L. Kruter  
Attorney, Agent, or Firm—Harris Zimmerman; Howard Cohen

[57] ABSTRACT

A surgical aspirator adaptable for body cavity or passageway use includes a handle having a vacuum passage extending longitudinally therethrough and a valve bore extending perpendicularly therethrough to receive a poppet in sealing fashion. The poppet includes sealing ribs protruding radially therefrom and extending longitudinally therealong to form a seal in the bore in any rotational position. The poppet also includes a radio-opaque pin which extends through the open port thereof. An aspirator tube is received in a bore in the handle, and is retained therein by the frictional engagement of an elongated hole in the aspirator tube which includes edges deformed radially outwardly therefrom to engage the bore. The distal end of the aspirator tube includes crossed slots extending therethrough and through adjacent side wall portions to prevent clogging thereof. An aspirator sheath is received concentrically about the aspirator tube, and includes a plurality of perforations therethrough to provide aspiration in body cavities. The sheath is joined to the aspirator tube by a detent slot formed therein with edges turned inwardly to frictionally engage the aspirator handle. The device is sufficiently simple to be readily sterilized for reuse, or to be fabricated in disposable form.

3 Claims, 34 Drawing Figures

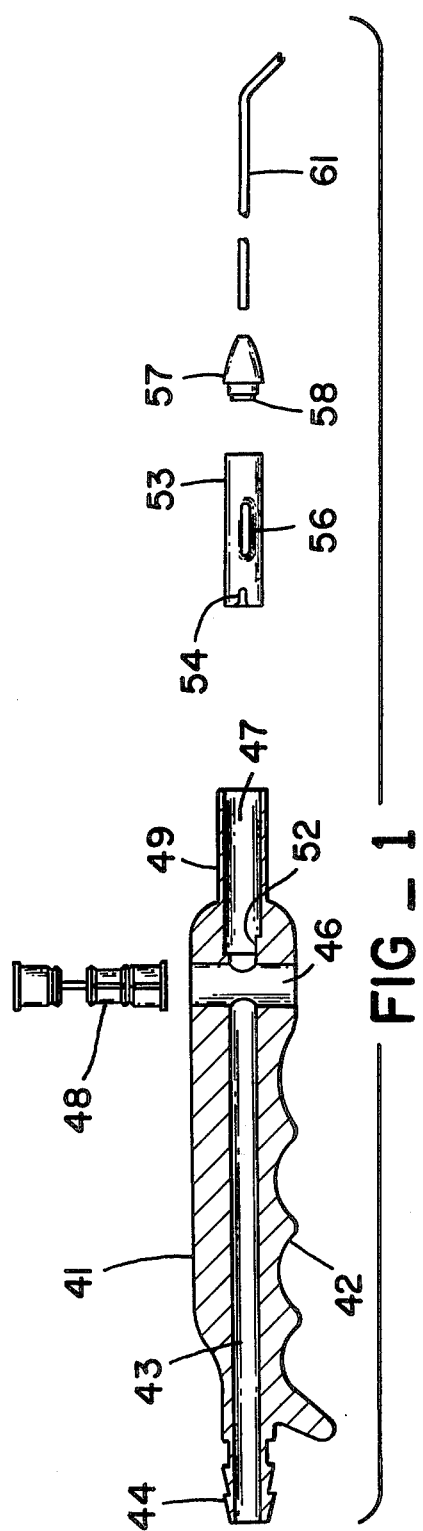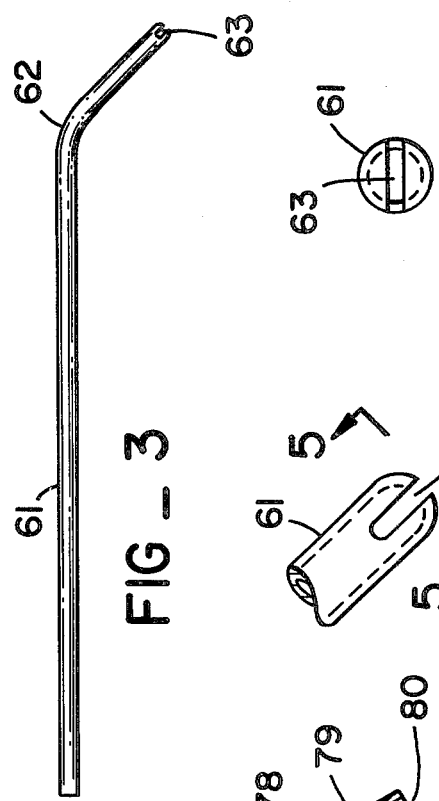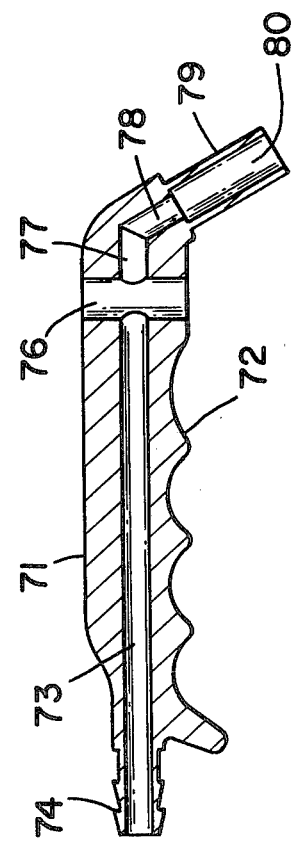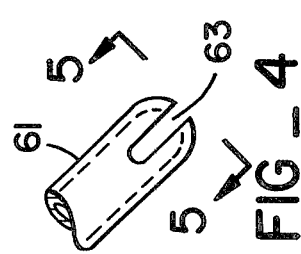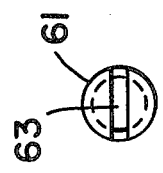

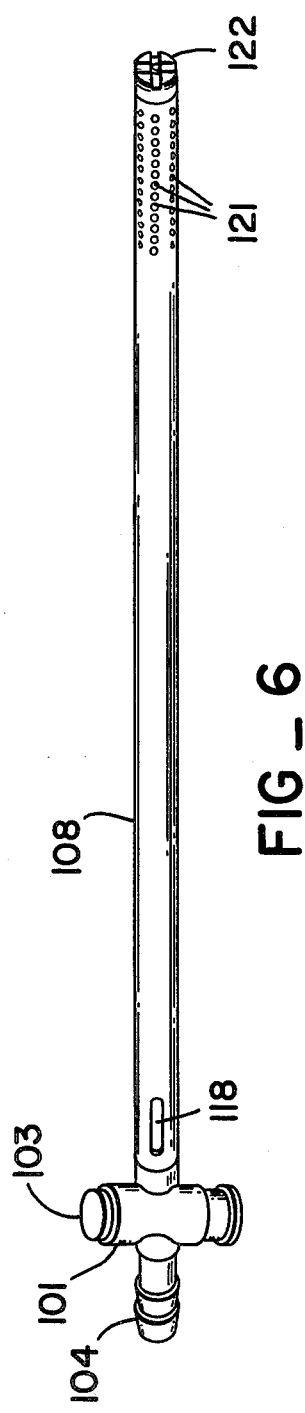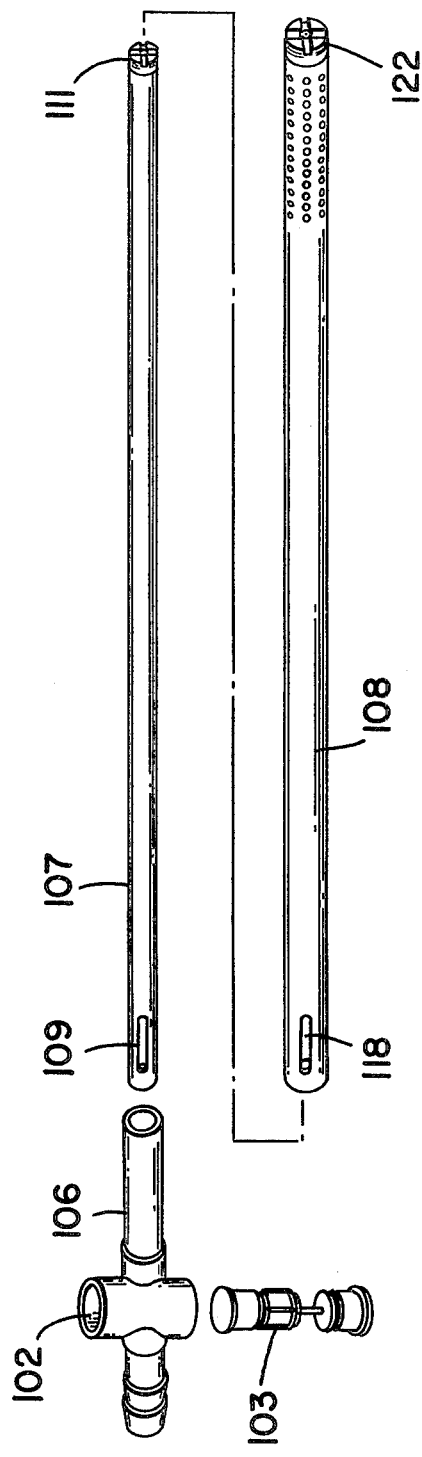

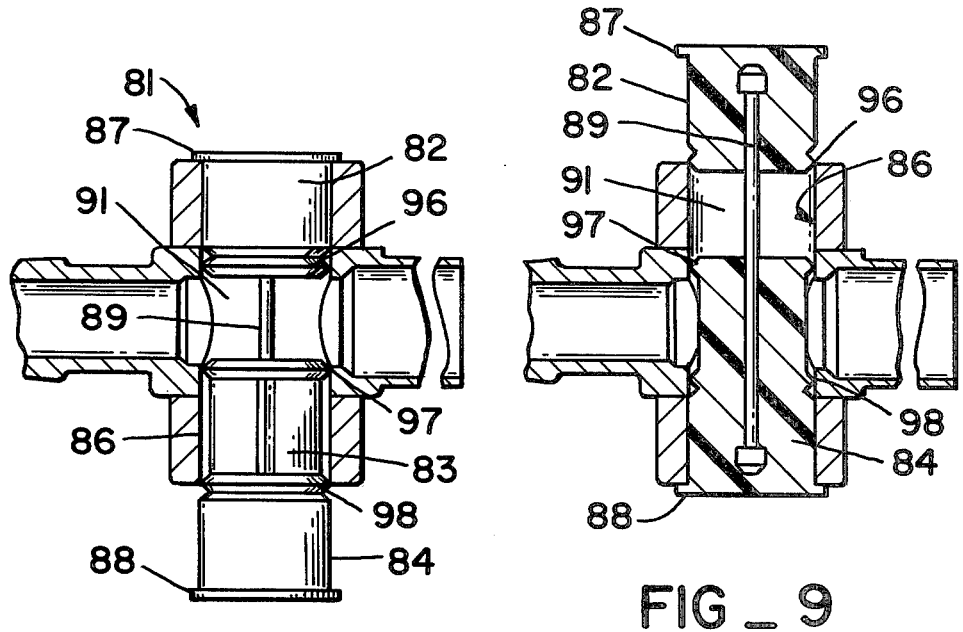
FIG_8
FIG_9
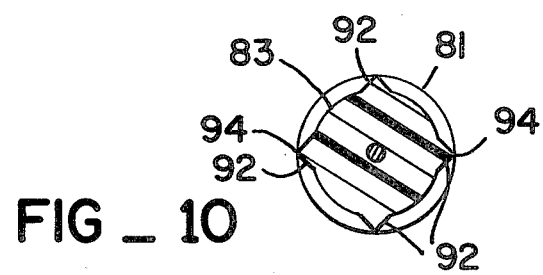
FIG_10
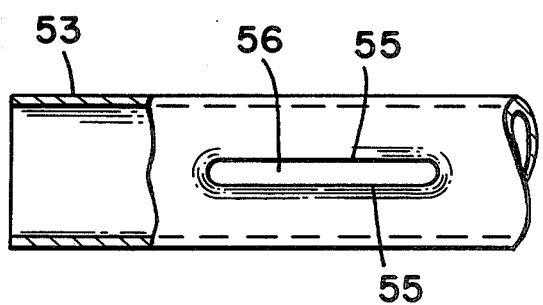
FIG_11
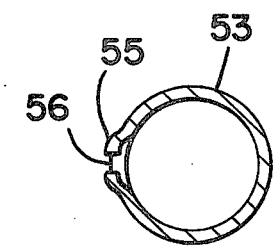
FIG_12

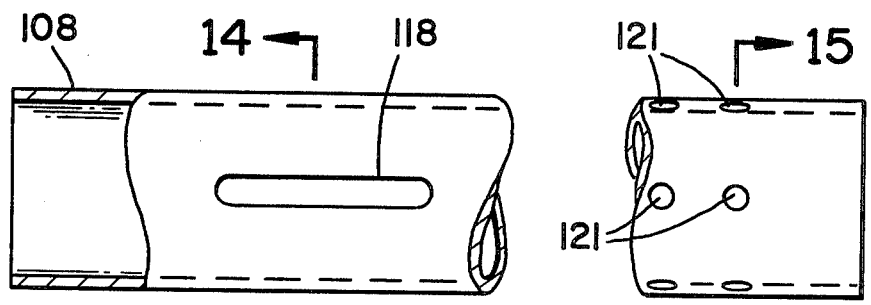
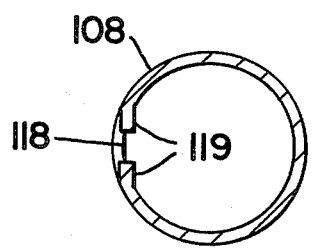
FIG_14
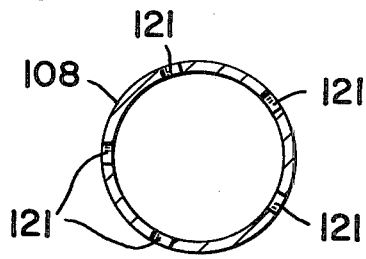
FIG_15
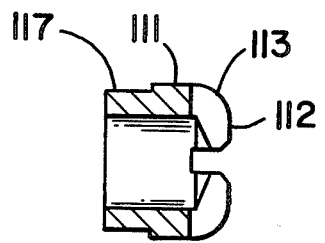
FIG_16
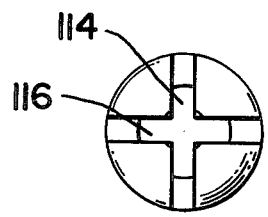
FIG_17
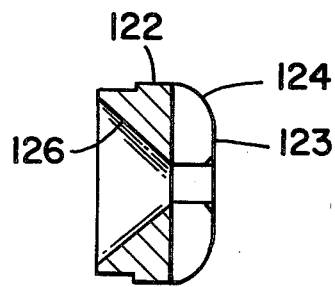
FIG_18
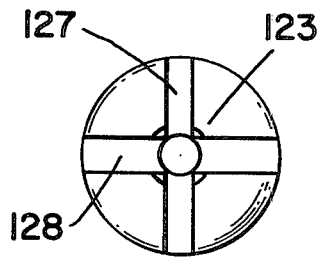
FIG_19

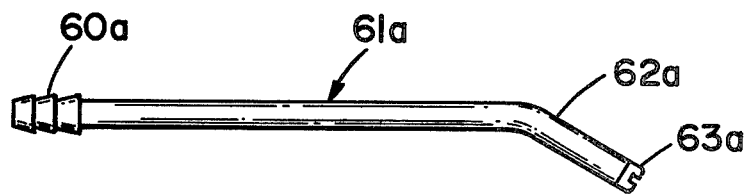
FIG _ 20
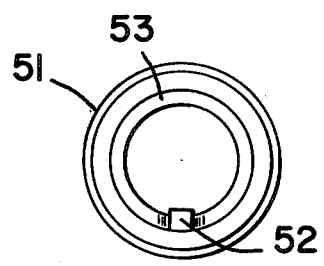
FIG _ 21
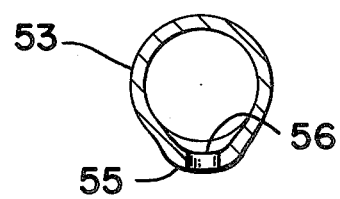
FIG _ 22
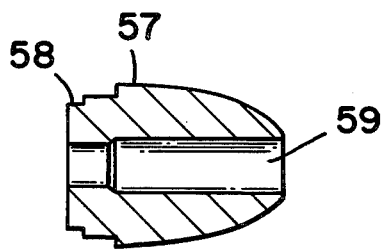
FIG _ 23
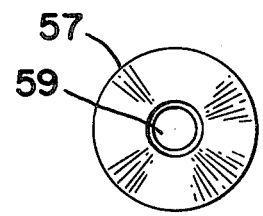
FIG _ 24

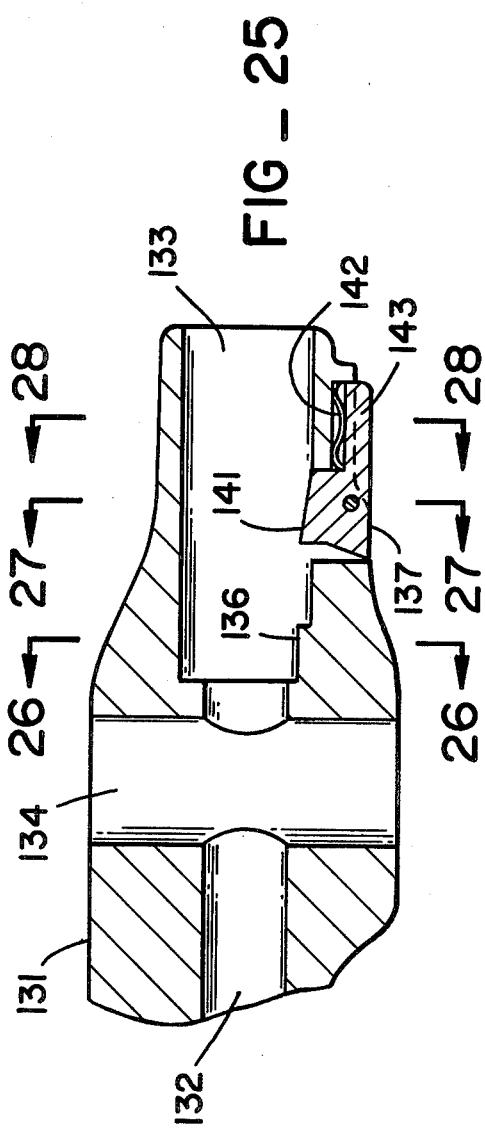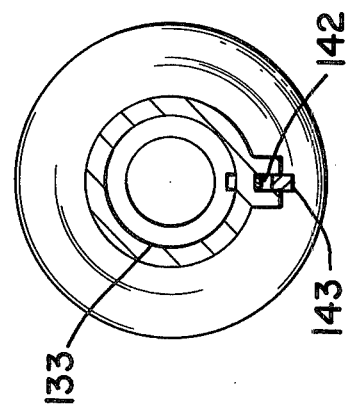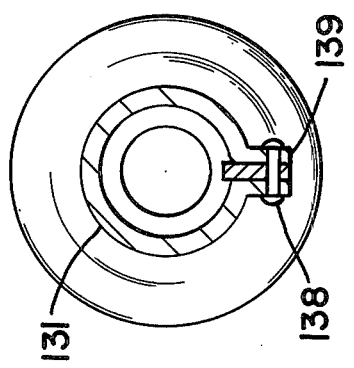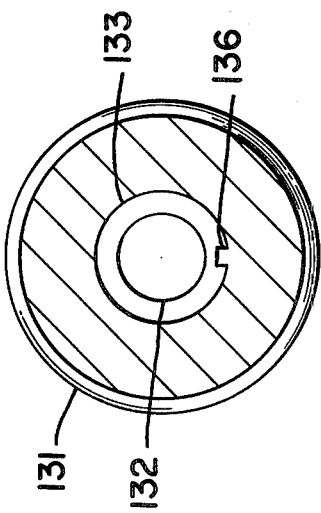

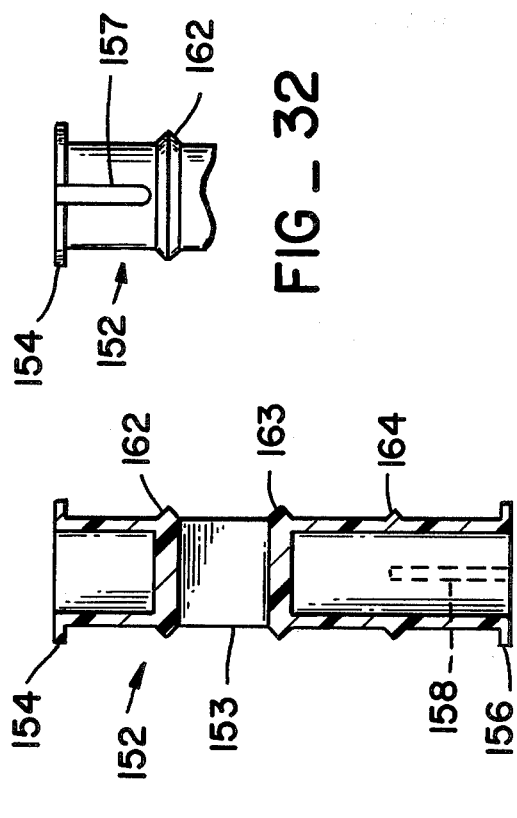
FIG_32
FIG_31
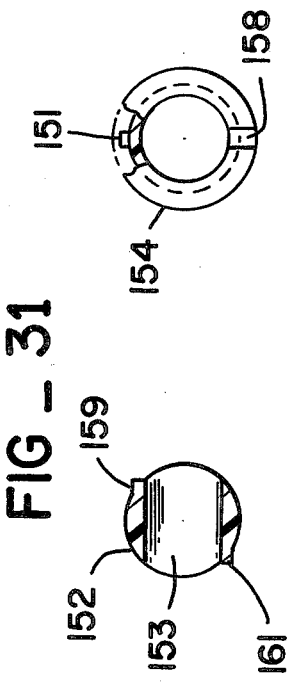
FIG_34
FIG_33
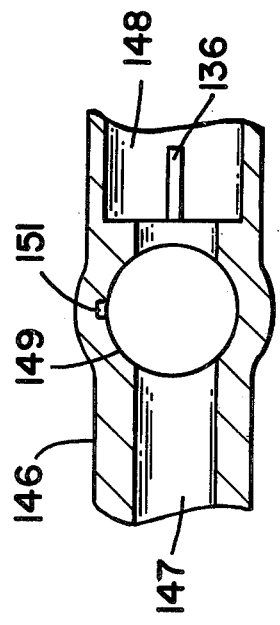
FIG_29
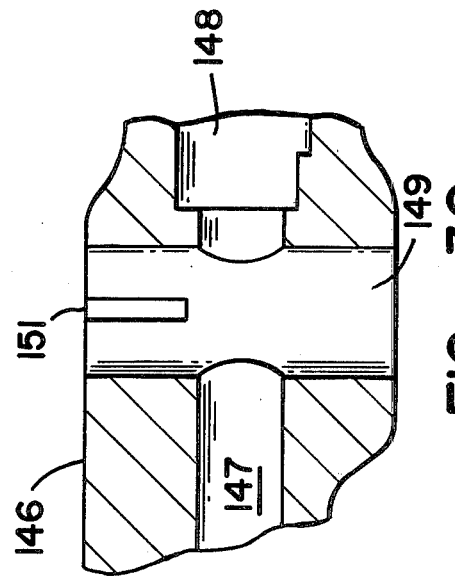
FIG_30

SURGICAL ASPIRATOR WITH POPPET CONTROL VALVE

BACKGROUND OF THE INVENTION

In many medical procedures and in most surgical procedures it is commonplace to employ vacuum aspiration to remove fluids and semi-fluid substances from the area of treatment or from the surgical site. Indeed, vacuum aspirator instruments are a common tool in the medical field, and are produced in a variety of forms for specific medical procedures and situations.

During surgery it is a common practice to dispose a vacuum aspirator in convenient access to the surgical site, and to maintain the aspirator in readiness to remove fluids from the surgical site as they accumulate therein. For reasons of convenience and speed, the aspirator is often placed in the operating condition; i.e., a vacuum source is applied thereto annd the aspirator is constantly drawing in ambient air in readiness for its occasional use in removing fluids from the surgical site. Unfortunately, this rather casual practice may cause unwitting contamination of the surgical wound, and may result in severe post-surgical complications.

When the vacuum aspirator instrument is operated continuously, the intake ports of the aspirator are exposed to a large volume of air which is drawn therein by the vacuum applied thereto. Although the ambient air in an operating room may be cleansed by filtering and by ultraviolet radiation, nonetheless it is known to contain a small population of both benign and malevolent bacteria. This low population or micro-organisms is generally insufficient to cause direct infection at the surgical site. However, a vacuum aspirator which constantly draws in large volumes of ambient air tends to act as a filter which removes some of the micro-organisms from the airstream and thereby forms a dense population of micro-organism at the intake ports of the aspirator. Indeed, the wetted condition of the aspirator, caused by immersion in the fluids which it is designed to remove from the body, may often increase the filtering effect of the aspirator. Recent research has shown that vacuum aspirator instruments may comprise a significant cause of post-operative infection and other complications. Indeed, this problem is described in U.S. Pat. No. 3,810,471, issued May 14, 1974.

The following patents comprise the closest known prior art:
U.S. Pat. No. 3,143,109
U.S. Pat. No. 3,335,727
U.S. Pat. No. 3,516,405
U.S. Pat. No. 3,645,497
U.S. Pat. No. 3,911,919
U.S. Pat. No. 3,958,573
U.S. Pat. No. 3,965,901
U.S. Pat. No. 3,991,762
German Pat. No. 2,446,470

The cited prior art discloses various vacuum aspirator arrangements for body cavities and body passages. Some of these aspirator devices employ valves which may be used by the physician to selectively control the operation of the aspirator. However, the valve arrangements disclosed in the prior art are generally too complex in design to be fashioned in disposable form, yet not sufficiently simple to be easily disassembled for cleaning and sterilization prior to reuse. It is also generally true that vacuum aspirators designed for body cavity use cannot be employed for body passage use without causing trauma to the body passage lining and associated tissued. Therefore, it is often required to employ more than one aspirator in the same surgical procedure. Furthermore, the valve system employed in the prior art aspirator devices are often difficult to manipulate between their on and off configurations. As a result, the surgeon or physican will tend to maintain the aspirator in the actuated condition as a matter of convenience, thereby exacerbating the problems mentioned in the foregoing discussion.

SUMMARY OF THE PRESENT INVENTION

The present invention generally comprises a vacuum aspirator for medical and surgical use which is uniquely designed to be adaptable for use in body cavities as well as in body passages. Other salient features of the present invention include a poppet valve which is provided to actuate the aspirator selectively only during actual use, so that contamination of the aspirator ports or tip is reduced to a minimum. The poppet valve of the present invention is designed for easy use, to encourage its use, and is also designed to be easily disassembled and cleaned for reuse. The present invention also features the ability to be converted quickly to a cavity aspirator or a passageway aspirator, due to the provision of concentric aspirator tubes which are retained by unique frictional detent slots.

The surgical aspirator adaptable for body cavity or passageway use includes a handle having a vacuum passage extending longitudinally therethrough and a valve bore extending perpendicularly therethrough to receive a poppet in sealing fashion. The poppet includes sealing ribs protruding radially therefrom and extending longitudinally therealong to form a seal in the bore in any rotational position, as well as annular sealing ribs which prevent inflow from the ends of the valve bore. The poppet also includes a radio-opaque pin which extends axially therethrough.

An aspirator tube is received in a bore in the handle, and is retained therein by the frictional engagement of an elongated hole in the aspirator tube which includes edges deformed radially outwardly therefrom to engage the bore. The distal end of the aspirator tube includes crossed slots extending therethrough and through adjacent side wall portions to prevent clogging thereof. An aspirator sheath is received concentrically about the aspirator tube, and includes a plurality of perforations therethrough to provide aspiration in body cavities. The sheath is joined to the aspirator tube by a detent slot formed therein with edges turned inwardly to frictionally engage the aspirator tube. Alternatively, a micro-tube aspirator assembly may be secured in the bore of the handle, the micro-tube having a small diameter and an obliquely bent distal end portion. The device is readily sterilized for reuse, and it is sufficiently simple in construction to be made in disposable form.

BRIEF DESCRIPTION OF THE DRAWING

FIG. 1 is an exploded view of one embodiment of the vacuum aspirator of the present invention.

FIG. 2 is a further embodiment of the handle portion of the vacuum aspirator shown in FIG. 1.

FIG. 3 is a further embodiment of the vacuum aspirator tube of the assembly shown in FIG. 1.

FIG. 4 is an enlarged detailed view of the tip of the aspirator tube shown in FIG. 3.

FIG. 5 is an end view of the aspirator tip of FIG. 4, taken along line 5—5 of FIG. 4.

FIG. 6 is a perspective view of a further embodiment of the vacuum aspirator of the present invention.

FIG. 7 is an exploded view of the vacuum aspirator embodiment of FIG. 6.

FIG. 8 is a cross-sectional view of one embodiment of the valve assembly of the vacuum aspirator of the present invention, the valve being disposed in the open, or flow through, position.

FIG. 9 is a cross-sectional view of the valve depicted in FIG. 8, shown in the closed or no flow position.

FIG. 10 is a lateral cross-sectional view of the valve poppet of the embodiment depicted in FIGS. 8 and 9.

FIG. 11 is an enlarged, detailed plan view of a detent slot according to the present invention.

FIG. 12 is a cross-sectional view of the detent slot depicted in FIG. 11.

FIG. 13 is a plan view of an aspirator sheath tube of the present invention.

FIG. 14 is a cross-sectional view taken along line 14—14 of FIG. 13.

FIG. 15 is a cross-sectional view taken along line 15—15 of FIG. 13.

FIG. 16 is a cross-sectional view view of one embodiment of an aspirator tip of the present invention.

FIG. 17 is an end view of the aspirator tip depicted in FIG. 16.

FIG. 18 is a cross-sectional view of another embodiment of an aspirator tip of the present invention.

FIG. 19 is an end view of the aspirator tip depicted in FIG. 18.

FIG. 20 is a partial cross-sectional view of a further embodiment of the aspirator tube assembly portion of the present invention.

FIG. 21 is an end view of the assembly depicted in FIG. 20.

FIG. 22 is a cross-sectional view of a detent slot according to the present invention.

FIG. 23 is a cross-sectional view of a further embodiment of an aspirator tip of the present invention.

FIG. 24 is an end view of the aspirator tip depicted in FIG. 23.

FIG. 25 is a partial cross-sectional view of a further embodiment of the handle portion of the present invention.

FIG. 26 is a cross-sectional view taken along 26—26 of FIG. 25.

FIG. 27 is a cross-sectional view taken along line 27—27 of FIG. 25.

FIG. 28 is a cross-sectional view taken along line 28—28 of FIG. 25.

FIG. 29 is a top cross-sectional view of a further embodiment of the control valve of the present invention.

FIG. 30 is a side cross-sectional view of the further embodiment depicted in FIG. 29.

FIG. 31 is a cross-sectional elevation of a further embodiment of the valve poppet of the present invention.

FIG. 32 is a detailed elevation of a portion of the valve poppet depicted in FIG. 31.

FIG. 33 is a lateral cross-sectional view of the valve poppet depicted in FIG. 31.

FIG. 34 is a partially cut-away end view of the valve poppet depicted in FIG. 31.

DESCRIPTION OF THE PREFERRED EMBODIMENT

The present invention generally comprises a vacuum aspirator for use in medical and surgical procedures. The most salient features of the present invention are its simplicity of design, which facilitates disassembly and cleaning of the unit for reuse, and its simple and effective one piece valve mechanism which provides selective control of the aspirator. As a result of the selective actuation of the aspirator, the volume of ambient air drawn therein is significantly reduced, and the concomitant contamination of the aspirator by air-borne contaminants is likewise reduced. The invention thus reduces the likelihood of post-surgical complications due to contamination of a surgical wound by a vacuum aspirator. Furthermore, one embodiment of the device easily may be interchangably converted between its body cavity aspirator configuration and its passageway aspirator configuration.

With reference to FIG. 1, one embodiment of the present invention includes a longitudinally extending handle 41 having a plurality of scalloped finger grips 42 extending along the ventral surface of the handle. A bore 43 extends longitudinally through the handle 41. A tubing nipple 44 extends from the rear end of the handle 41 to secure a resilient tubing thereto which is connected to a vacuum source. Thus the bore 43 is likewise connected to the vacuum source.

The handle 41 also includes a valve bore 46 extending generally vertically through the handle and disposed generally transversely with respect to the bore 43. A counter-bore 47 extends inwardly into the front end of the handle 41, and is disposed in open flow communication with the valve bore 46. A valve poppet 48 is secured within the bore 46 to selectively block or complete the flow path extending between the counter-bore 47 and the vacuum bore 43. The poppet 48 is longer in its axial dimension than the axial length of the bore 46, so that a portion of the poppet extends outwardly from the upper or lower end of the bore 46. The poppet is actuated by manual pressure exerted on the portion of the poppet extending from the bore to translate the poppet into the open or closed position. In the configuration of FIG. 8, the valve poppet 48 is in the closed position when the poppet extends upwardly from the upper end of the bore 46, and may be translated to the open position by pushing downwardly with manual pressure on the upper end of the poppet so that the lower end of the poppet extends from the lower end of the bore 46.

The handle 41 also includes a hollow, tubular extension 49 extending forwardly of the handle and including the counterbore 47 extending therethrough. The inner end portion of the counterbore also includes a locating rib 52 extending radially inwardly into the bore for purposes to be explained in the following description.

The invention further includes a hollow tubular adapter member 53 which is dimensioned to be received within the bore 47 of the tubular extension 49. The adapter member 53 includes a slot 54 extending in the tubular wall from the rear end thereof. The slot 54 is disposed to engage the inner extent of the locating rib 52 to prevent rotation of the adapter 53 within the tubular member 49. The member 53 also includes a unique detent arrangement comprising a slot 56 extending longitudinally in a medial portion thereof. As shown in FIGS. 11 and 12, the slot 56 is long and narrow with ends of small radius, and the edge portions 55 of the slot 56 are deformed radially outwardly from the axis of the adapter tube. The edge portions 55 thus impinge upon the inner bore of the tubular member 49 and create a frictional engagement therewith which retains the member 53 within the member 49. The detent slot 56 and the edges 55 permit the member 53 to be assembled to or removed from the tubular member 59 by manual effort. An adaptor tip 57 includes a rear end 58 which is dimensioned to be press-fit into the bore of the adapter tube 53. As shown in FIGS. 23 and 24, the adaptor tip 57 includes a bore 58 extending axially therethrough.

The rear end of a narrow aspirator tube 61, as shown in FIG. 3, is received within the bore 59 of the tip 57 in press-fit relationship. The tube 61 includes an oblique bend 62 in a forward portion thereof, and also includes an aspirator slot 63 in the forward end thereof. As shown in FIGS. 4 and 5, the slot 63 extends diametrically across the hemispherical end of the tube 61, and also extends axially into the tubular side wall of the member. The axial extent of the slot 63 is provided to avoid clogging and blockage of the slot by solid or semi-solid debris which may be drawn into the aspirator during aspiration procedures.

A further embodiment of the handle of the present invention, depicted in FIG. 2, comprises a handle member 71 which extends longitudinally and includes scalloped finger grips 72 extending longitudinally along the ventral portion thereof. A vacuum bore 73 extends axially through the longitudinal extent of the handle, with a resilient tubing nipple 74 extending rearwardly from the handle and providing flow communication to the bore 73 and a vacuum tube secured thereto. It may be appreciated that these portions of the handle 71 are substantially similar to the previous embodiment, as is the provision of a valve bore 76 extending transversely through the bore 73 in a forward portion of the handle member. A bore 77 extends forwardly from the valve bore 76, and includes a dog leg portion 78 extending obliquely downwardly from the forward end of the handle member 71. Extending forwardly from the handle is a tubular extension member 79, with a counter-bore 80 extending therethrough, as in the previous embodiment, so that the aspirator tip assembly, comprising the aspirator tube 61, the tip 57, and the adapter tubing 53 may extend downwardly in oblique fashion from the handle member 71. This disposition of the aspirator assembly alleviates manual fatigue for the surgeon in those situations in which the aspirator assembly must be disposed in an obliquely downwardly extending fashion for extended periods of time.

A novel feature of the present invention is the construction of the poppet valve 48, which provides complete control of the vacuum aspiration provided by the present invention through the use of one moving part and no other ancillary parts, seals, rings, or the like. With reference to FIGS. 8 and 9, one embodiment of the poppet valve comprises a poppet 81 having an upper cylindrical portion 82, a lower medial cylindrical portion 83, and a lower cylindrical portion 84. Each of the portions 82, 83, and 84 are cylindrical solid members formed of a resilient substance, each portion being substantially equal in axial extent. The diameter of the portions 82 and 84 is slightly less than the valve bore 86 in which the poppet is disposed, so that the portions 82 and 84 are slidably received within the bore. A pair of flanges 87 and 88 extend radially outwardly from the opposed ends of the portions 82 and 84, respectively.

The flanges 87 and 88 comprise stop members which retain the poppet within the bore.

The upper portion 82 is joined to the lower portions 83 and 84 by a valve pin 89 which extends axially into the portions 82-84 and is fixedly secured therein. As shown in FIGS. 8 and 9, the pin 89 maintains the upper portion 82 in axially spaced relationship with respect to the portions 83 and 84, thereby defining a valve port 91 through which a vacuum may be applied to the aspirator tip assembly, and through which fluid, surgical debris, and the like may be drawn.

In the disposition depicted in FIG. 8, the valve port 91 is aligned with the valve bore and counter-bore, and the valve is disposed in the open, flow through position. In this position the lower portion 84 extends downwardly and outwardly of the valve bore, so that it may be actuated by manual pressure. In the disposition depicted in FIG. 9, the poppet medial portion 83 is disposed to block the flow path between the bore and counter-bore, and the poppet is thus in the closed position. The closed position may be reached by manual pressure on the lower portion 84 when the valve is in the open position. In the closed position the upper poppet portion 82 is extended axially outwardly of the valve bore, and is disposed for manual impingement to return the valve to the open position of FIG. 8.

The nominal diameter of the lower medial portion 83 of the poppet 81 is less than the diameters of the portions 82 and 84. However, the portion 83 includes a quartet of ribs 92 protruding radially outwardly from the portion 83 and extending longitudinally the length thereof in parallel relationship to the axis thereof. The ribs 92 are spaced equally about the periphery of the portion 83, and each includes a distal edge 94 extending longitudinally and adapted to impinge upon the bore 86. The diametrical spacing of diametrically opposed edges 94 is slightly greater than the diameter of the bore 86, so that the edges 94 impinge upon the bore in compressive, sealing fashion. Due to the angular spacing of the ribs 92, it is assured that two of the diametrically opposed ribs will impinge upon the side walls of the bore 86 when the portion 83 is disposed in the closed position of FIG. 9, regardless of the rotational disposition of the poppet. Thus there is no preferred angular disposition of the poppet 81 in the bore 86, and the poppet may be inserted at any rotational angle and turned to any angle without affecting the performance of the valve.

The poppet 81 also includes a trio of annular ribs 96, 97, and 98 disposed at the lower end of the portion 82, and at the upper and lower ends of the portion 83, respectively, of the poppet. The annular ribs are provided with annular edges extending continuously thereabout and impinging compressively upon the bore 86 to prevent any air flow thereby. The spacing of the annular ribs is such that the bore 86 is sealed at its upper and lower extremities regardless of the position of the poppet 81.

It may be appreciated that the valve of the present invention consists solely of one component, the poppet 81, and that there are no further fixed or moving parts required to achieve the valving action which controls the vacuum aspirator. Thus, it is extremely simple to disassemble the valve by removing the poppet from the bore by strong manual pressure for cleaning and sterilization thereof. The poppet may be returned to the bore and reused in this fashion indefinitely. There are no other parts required to be replaced, and no tools required for these procedures.

Furthermore, the pin 89 is formed of a radio opaque substance, such as stainless steel, which is easily imaged by X-ray means. Should the valve poppet 81 be inadvertently lost within a surgical site, the presence and location of the poppet easily may be determined due to the presence of the radio opaque pin 89.

A further embodiment of the present invention, depicted in FIGS. 6 and 7, includes a valve body 101 having a valve bore 102 extending therethrough and adapted to receive a valve poppet 103 therein. The valve poppet 103 may be substantially similar to the poppet 81 described in the foregoing, or may comprise any embodiment of the poppet disclosed herein. A resilient tubing nipple 104 extends from one side of the valve body 101, and a fixed hollow tubular member 106 extends from the other side of the valve body in diametrically opposed fashion to the nipple 104. The members 104 and 106 are disposed on a longitudinal axis which is substantially perpendicular to the axis of the valve bore 102. It may be appreciated that the valve body 101 may be grasped manually, and that the poppet 103 may be actuated by finger pressure to open or close a fluid flow path between the members 104 and 106. The member 104 is connected by resilient tubing to a vacuum source.

The present embodiment also includes a pair of aspirator tubes 107 and 108, either of which may be joined to the hollow tubular member 106. The member 107 is dimensioned to be slidably received with in the tubular member 106, and includes a detent slot 109 at the rear end thereof. The slot 109 is substantially similar to the slot 56 depicted in FIGS. 11 and 12, and includes outwardly deformed edge portions which frictionally engage the bore of the tubular member 106 to retain the tube 107 therein. Joined to the forward end of the tube 107 is an aspirator tip 111.

As shown in FIGS. 16 and 17, the aspirator tip 111 includes a generally planar forward face 112 extending orthogonally with respect to the axis of the tube 107 and including a large radius 113 which extends to the cylindrical side wall of the tip. A pair of diametrical slots 114 and 116 extend into the face 112 and are disposed to intersect each with the other in orthogonal fashion. The slots 114 and 116 are sufficiently deep to extend slightly into the cylindrical side wall of the tip; the depth of the slots into the side wall is designed to prevent clogging of the slots by solid debris or tissue. The rear end of the tip 111 includes a reduced diameter annulus 117 which frictionally engages the forward end of the bore of the tube 107. The tip 111 is particularly adapted for aspiration of a narrow body passage.

The embodiment of FIGS. 6 and 7 easily may be converted to provide aspiration within a body cavity. This may be accomplished by securing the tubular member 108 concentrically about the tubular member 107, and securing the member 108 to the outer surface of the member 106.

As shown in FIGS. 13-15, the member 108 includes a detent slot 118 disposed in the rear end portion thereof. The edge portions 119 are crimped inwardly to frictionally engage the outer peripheral surface of the member 106 and thereby retain the tube 108 thereabout. It may be appreciated that the detent slot 118 secures the members together with no moving parts, and that the detent slot is easily cleaned and sterilized for reuse. The forward end of the tube 108 includes a large plurality of intake holes 121 extending in longitudinal rows which are angularly spaced about the forward end of the member. The large number of intake holes assures that the aspirator intake will not be blocked by adjacent tissue or the like.

Joined to the forward end of the tube 108 is an aspirator tip 122. As shown in FIGS. 18 and 19, the tip 122 includes a generally flat end face 123 which merges with the side wall of the tip through a large radius 124. The inner bore of the tip 122 is provided with a truncated, conical taper 126. A pair of orthogonally related slots 127 and 128 extend into the face 123 of the tip, the intersection of the slots forming an opening in the face 123 which extends to the forward truncated open end of the taper 126. The slots 127 and 128 do not extend sufficiently deeply into the tip to enter the side walls thereof, as there is no need for protection against clogging of the tip. This is due to the presence of the plurality of side intake ports 121 in the tube 108.

It may be appreciated that the member 108 may be disposed concentrically about the member 107, to convert the present embodiment from a passageway aspirator to a cavity aspirator. Furthermore, it may be noted that the aspirator tubes 107 and 108, together with their respective tips 111 and 122, may be used advantageously in conjunction with the embodiments depicted in FIGS. 1 and 2, that is, the tubes 107 and/or 108 may be joined to the tubular member 49 of the previous embodiment to render that embodiment convertible from cavity aspiration to passageway aspiration in a like manner.

With reference to FIGS. 25-28, a further embodiment of the present invention includes a portion 131 of a handle member such as the member 41 depicted in FIG. 1. The handle portion 131 includes a bore 132 extending longitudinally therein, and a counterbore 133 exending into the forward end of the handle. As before, a transverse valve bore 134 extends into the handle portion 131 perpendicularly with respect to the bore 132 and counterbore 133, and joining those two passages. The bore 134 is adapted to receive a valve poppet as described herein.

The inner end of the counterbore 133 includes a lip 136 protruding radially inwardly from the inner surface of the counterbore and disposed to engage a locating slot of an adapter tube, such as the slot 54 of the tube 53 depicted in FIG. 1. The present embodiment also includes a detent member 137 which is pivotally joined to the handle portion 131 by a pivot pin 138 extending through a ventrally protruding boss 139 of the handle portion 131. The detent member 137 is disposed within a slot formed in the boss 139, and the detent member includes an inner portion 141 which protrudes slightly into the bore 133. A leaf spring 142 is disposed between a forwardly extending lever portion 143 of the detent member and an inner portion of the slot to bias the detent member so that the portion 141 extends into the bore 133.

The inner end 141 of the detent member 137 is adapted to engage a detent slot, according to the present invention, of any of the aspirator tubes disclosed herein. For example, the detent portion 141 may engage the slot 56 of the tubular adaptor member 53, to retain the member 53 within the bore 133. This detent arrangement provides positive retention of any aspirator tube assembly of the present invention, so that the frictional engagement provided by any of the detent slots according to the invention is augmented by the positive mechanical engagement of the portion 141 within the detent slot. It may be appreciated that the mechanical engagement easily may be released by manually urging the lever end 143 inwardly to release the inner portion 141 from the detent slot.

The present invention also provides a simplified embodiment of the aspirator tube assembly, as shown in FIG. 20. An aspirator tube 61a comprises a longitudinally extending hollow tubular member having an end 60a which is provided with truncated conical surfaces in serial adjacent relationship to form annular barbs. A forward portion of the tube 61a includes an oblique bend 62a, and an aspirator tip 63a is received in the forward end of the tube. The tube 61a is designed to be secured directly to any of the handle embodiments disclosed herein, the barbed end 60a being self-retaining in any of the counterbores 47, 80, or 106. The simplicity of this embodiment renders it suitable for fabrication from disposable materials.

A further embodiment of the poppet valve assembly of the present invention, depicted in FIGS. 29-34, includes a handle portion 146 having a vacuum bore 147 extending longitudinally therein and a counter bore 148 adapted to receive an aspirator tube assembly. A valve bore 149 extends through the handle portion 146 transversely with respect to the bore 147 and counterbore 148, joining the latter bores in flow communication. The bore 149 includes a guide slot 151 extending parallel to the axis of the bore in the upper portion thereof and protruding radially outwardly from the surface of the bore.

The valve assembly of the present embodiment also includes a valve poppet 152, generally comprising a unitary cylindrical member formed of a resilient substance and being substantially hollow throughout its axial extent. However, a valve port 153 extends through the member 152 transversely with respect to the axis thereof, and disposed to connect the bore 147 and 148 in open flow communication when aligned therewith.

As in the previous poppet embodiment, a pair of flanges 154 and 156 extend radially outwardly from opposed ends of the member 152, and are greater in diameter than the diameter of the bore 149. The flanges thus serve to retain the poppet within the valve bore. The poppet 152 also includes a guide rib 157 protruding radially from an upper portion of the poppet and extending longitudinally parallel to the axis thereof. The rib 157 is disposed to engage the slot 151, thereby preventing rotation of the poppet 152 within the bore 149. In a lower portion of the poppet, a slot 158 extends longitudinally in the side wall of the hollow portion of the member 152, so that the lower end of the poppet may be compressed in diameter and inserted into the upper portion of the bore 149. When the member 152 is fully inserted into the bore, and the flange 156 extends from the lower end thereof, the resilient nature of the material which forms the poppet will cause it to expand and substantially fill the bore 149.

The poppet 152 also includes a pair of diametrically opposed, longitudinally extending ribs 159 and 161 which protrude radially outwardly from the generally cylindrical surface of the poppet. The ribs 159 and 161 serve the same purpose as the ribs 92 of the previous poppet embodiment, and are disposed to compressively engage the inner surface of the bore 149 in a like manner to effect a seal therewith. Due to the fact that the poppet 152 cannot rotate within the bore 149, the one pair of diametrically opposed ribs 159 and 161 are sufficient to seal the poppet within the bore and prevent any significant fluid flow or gaseous flow thereby.

The poppet 152 also includes a trio of annular ribs 162, 163, and 164, the first two being disposed directly adjacent to the upper extent and lower extent of the valve port 153, respectively. The annular rib 164 is disposed about a lower medial portion of the member 152. The ribs 162-164 are disposed to impinge compressively on the surface of the bore 149 to effect a seal therewith in a longitudinal direction, in a manner substantially similar to the annular seals 96-98 of the previous embodiment depicted in FIGS. 8 and 9. Indeed, the spacing of the annular ribs 162-164 in the axial direction is substantially the same as the spacing of the previous embodiment. However, the valve poppet 152 is constructed to be disposable rather than reusable, and is not adapted easily to be removed from the bore 149. However, the valve portion 153 provides a totally unobstructed flow path from the counter-bore 148 to the vacuum bore 147, thereby providing no obstruction upon which debris might lodge.

It may be appreciated that the latter embodiment of the poppet valve assembly may be incorporated with any of the other embodiments of the handle, or of the aspirator tube assemblies and tips.

The various embodiments of the present invention described in the foregoing illustrate the salient and novel features of the invention. For example, the vacuum aspirator according to the present invention is easily adapted to be either a cavity or passageway aspirator. The one piece valve mechanism is so simple to use that it encourages physicians and surgeons to actuate the aspirator only when necessary, thereby minimizing the problem of airborne contamination of the aspirator tip. Furthermore, the one piece valve construction is sufficiently simple to be easily disassembled for cleaning and sterilization, or to be fabricated in disposable form.

I claim:

1. A vacuum aspirator, comprising handle means connected to a vacuum source, aspirator tip means extending from said handle means, and poppet valve means disposed between said aspirator tip means and said vacuum source to selectively establish or break flow communications therebetween, said handle means including a handle member extending longitudinally, a vacuum passageway extending longitudinally through said handle member along a first axis, said poppet valve means including a valve bore extending through said handle member along a second axis and intersecting said vacuum passageway, said first and second axes being generally orthogonal, said poppet valve means further including a generally cylindrical poppet slidably retained in said valve bore and received therein at any rotational angle about said second axis of said bore, said poppet being formed in integral, one-piece construction, said poppet further including a valve port extending therethrough, said poppet being slidably translatable in said valve bore to selectively dispose said valve port in flow communication with said vacuum passageway and said aspirator tip means, said poppet including seal means for securing said poppet in said valve bore in slidable, sealing fashion, said poppet including a first resilient cylindrical portion and a second resilient cylindrical portion, said first and second portions being axially spaced apart to define a fixed spacing therebetween, said valve port extending through said fixed spacing, a valve pin extending generally parallel to said second axis between said first and second portions to maintain said fixed spacing, said valve pin being radioopaque, said seal means including a plurality of annular ribs formed integrally with and protruding radially outwardly from said poppet and spaced axially therealong, a pair of said annular ribs being disposed at opposed ends of each of said first and second portions and adapted to compressively engage the inner surface of said valve bore in pressure-sealing fashion, said seal means further including a plurality of longitudinal ribs extending integrally and radially outwardly from each of said first and second cylindrical portions and extending the entire length of each, said longitudinal ribs disposed parallel to said second axis and adapted to impinge compressively on the inner surface of said valve bore to form a pressure seal therewith, said poppet including a pair of stop flanges extending radially outwardly from opposed ends thereof and having outer diameters greater than the diameter of said valve bore.

2. The vacuum aspirator of claim 1, wherein said longitudinal ribs extend parallel to the axis of said valve bore and are angularly spaced about the circumference of said poppet to seal said valve bore and prevent fluid flow between said aspirator tip means and said vacuum passageway when said poppet is in any angular disposition about said axis of said valve bore.

3. The vacuum aspirator of claim 1, said handle means including a tubular extension protruding therefrom, said aspirator tip means including first and second tubes disposed concentrically with respect to said first axis and engageable with said tubular extension, said first aspirator tube being adapted for passageway aspiration, and said second aspirator tube being adapted for body cavity aspiration, said first tube being removably secured at one end within said tubular extension, said second tube being removably received at one end about said tubular extension, said first and second tubes being selectively removable for use either individually or in combination.

* * * * *